United States Patent
Bloom et al.

(10) Patent No.: US 9,023,040 B2
(45) Date of Patent: May 5, 2015

(54) ELECTROSURGICAL CUTTING DEVICES

(75) Inventors: Eliot F. Bloom, Hopkinton, NH (US);
Denise C. Lane, North Andover, MA (US); Vaclav O. Podany, Dover, NH (US); Brian M. Conley, South Berwick, ME (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1227 days.

(21) Appl. No.: 12/912,659

(22) Filed: Oct. 26, 2010

(65) Prior Publication Data

US 2012/0101489 A1    Apr. 26, 2012

(51) Int. Cl.
*A61B 18/14* (2006.01)
*A61B 18/00* (2006.01)

(52) U.S. Cl.
CPC ... *A61B 18/1492* (2013.01); *A61B 2018/00601* (2013.01); *A61B 2018/1407* (2013.01); *A61B 2218/007* (2013.01)

(58) Field of Classification Search
CPC ...... A61B 18/04; A61B 18/08; A61B 18/082; A61B 18/12; A61B 18/14; A61B 18/1402; A61B 18/1477; A61B 18/148; A61B 18/1487; A61B 18/1492; A61B 2018/00601; A61B 2018/00607; A61B 2018/1405; A61B 17/32; A61B 17/3205; A61B 17/32053; A61B 17/3207; A61B 17/320725; A61B 17/34; A61B 17/3494; A61B 2017/32
USPC .............................. 606/32–34, 37, 39, 41–49
See application file for complete search history.

(56) References Cited

U.S. PATENT DOCUMENTS

| | | | |
|---|---|---|---|
| 2,888,928 | A | 6/1959 | Seiger |
| 3,682,130 | A | 8/1972 | Jeffers |

(Continued)

FOREIGN PATENT DOCUMENTS

| | | |
|---|---|---|
| WO | WO96/04955 A2 | 2/1996 |
| WO | WO 98/46119 A1 | 10/1998 |

(Continued)

OTHER PUBLICATIONS

International Search Report and Written Opinion for International Appl. No. PCT/US2011/057643, European Patent Office, The Netherlands, mailed on Apr. 12, 2012, 10 pages.

(Continued)

*Primary Examiner* — Michael Peffley
*Assistant Examiner* — Khadijeh Vahdat
(74) *Attorney, Agent, or Firm* — Jeffrey J. Hohenshell

(57) ABSTRACT

A cutting device for tissue separation includes a cutting edge using electrical energy such as RF power that is coupled to, but thermally insulated from, a catheter in an elongated medical device. Thermal insulation between a ring-type cutting device and the catheter is provided by a gap, slots within the ring, and/or slanted slots within the ring. In one embodiment, tissue separation occurs by rotation of a ring-type electrically-powered cutting edge having internal cross-bar elements. In an alternate embodiment, tissue separation occurs by longitudinal movement of an offset electrically-powered cutting edge that is pressed against tissue by an inflatable balloon. In a further alternate embodiment, a cutting edge is coupled longitudinally to a catheter, is provided electrical energy by wired connection to the braided catheter, but is thermally isolated from the catheter.

14 Claims, 11 Drawing Sheets

(56) References Cited

U.S. PATENT DOCUMENTS

| | | |
|---|---|---|
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,671,274 A | 6/1987 | Scrochenko |
| 4,736,749 A | 4/1988 | Lundback |
| 4,779,611 A | 10/1988 | Grooters et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,047,027 A | 9/1991 | Rydell |
| 5,047,028 A | 9/1991 | Qian |
| 5,190,541 A | 3/1993 | Abele et al. |
| 5,195,959 A | 3/1993 | Smith |
| 5,197,963 A | 3/1993 | Parins |
| 5,254,117 A | 10/1993 | Rigby et al. |
| 5,281,215 A | 1/1994 | Milder |
| 5,287,845 A | 2/1994 | Faul et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,372,603 A | 12/1994 | Acker et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Milder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,700 A | 4/1996 | Leone et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,679 A | 7/1996 | Fram et al. |
| 5,542,916 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,604 A * | 8/1996 | Sutcu et al. ..................... 606/45 |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,607,422 A | 3/1997 | Smeets et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |

(56) References Cited

U.S. PATENT DOCUMENTS

| | | | |
|---|---|---|---|
| 5,697,882 | A | 12/1997 | Eggers et al. |
| 5,697,925 | A | 12/1997 | Taylor |
| 5,697,927 | A | 12/1997 | Imran et al. |
| 5,697,928 | A | 12/1997 | Walcott et al. |
| 5,713,942 | A | 2/1998 | Stern |
| 5,716,389 | A | 2/1998 | Walinsky et al. |
| 5,718,241 | A | 2/1998 | Ben-Haim et al. |
| 5,718,701 | A | 2/1998 | Shai et al. |
| 5,720,775 | A | 2/1998 | Larnard |
| 5,722,402 | A | 3/1998 | Swanson et al. |
| 5,730,074 | A | 3/1998 | Peter |
| 5,730,127 | A | 3/1998 | Avitall |
| 5,730,704 | A | 3/1998 | Avitall |
| 5,733,280 | A | 3/1998 | Avitall |
| 5,735,280 | A | 4/1998 | Sherman et al. |
| 5,735,290 | A | 4/1998 | Sterman et al. |
| 5,743,903 | A | 4/1998 | Stern et al. |
| 5,746,224 | A | 5/1998 | Edwards |
| 5,755,760 | A | 5/1998 | Maguire et al. |
| 5,769,846 | A | 6/1998 | Edwards et al. |
| 5,782,828 | A | 7/1998 | Chen et al. |
| 5,785,706 | A | 7/1998 | Bednarek |
| 5,788,636 | A | 8/1998 | Curley |
| 5,792,140 | A | 8/1998 | Tu et al. |
| 5,797,905 | A | 8/1998 | Fleischman et al. |
| 5,797,960 | A | 8/1998 | Stevens et al. |
| 5,800,428 | A | 9/1998 | Nelson et al. |
| 5,800,482 | A | 9/1998 | Pomeranz et al. |
| 5,810,764 | A | 9/1998 | Eggers et al. |
| 5,810,802 | A | 9/1998 | Panescu et al. |
| 5,810,806 | A * | 9/1998 | Ritchart et al. ............... 606/45 |
| 5,827,216 | A | 10/1998 | Igo et al. |
| 5,836,947 | A | 11/1998 | Fleischman et al. |
| 5,840,030 | A | 11/1998 | Ferek-Petric et al. |
| 5,843,021 | A | 12/1998 | Edwards et al. |
| 5,843,152 | A | 12/1998 | Tu et al. |
| 5,844,349 | A | 12/1998 | Oakley et al. |
| 5,846,187 | A | 12/1998 | Wells et al. |
| 5,846,191 | A | 12/1998 | Wells et al. |
| 5,849,028 | A | 12/1998 | Chen |
| 5,861,021 | A | 1/1999 | Thome et al. |
| 5,871,523 | A | 2/1999 | Fleischman et al. |
| 5,871,525 | A | 2/1999 | Edwards et al. |
| 5,873,845 | A | 2/1999 | Cline et al. |
| 5,873,855 | A | 2/1999 | Eggers et al. |
| 5,876,399 | A | 3/1999 | Chia et al. |
| 5,879,295 | A | 3/1999 | Li et al. |
| 5,879,296 | A | 3/1999 | Ockuly et al. |
| 5,879,348 | A | 3/1999 | Owens et al. |
| 5,881,732 | A | 3/1999 | Sung et al. |
| 5,882,346 | A | 3/1999 | Pomeranz et al. |
| 5,885,278 | A | 3/1999 | Fleischman |
| 5,891,142 | A | 4/1999 | Eggers et al. |
| 5,893,848 | A | 4/1999 | Negus et al. |
| 5,895,355 | A | 4/1999 | Schaer |
| 5,895,417 | A | 4/1999 | Pomeranz et al. |
| 5,897,553 | A | 4/1999 | Mulier |
| 5,897,554 | A | 4/1999 | Chia et al. |
| 5,899,898 | A | 5/1999 | Arless et al. |
| 5,899,899 | A | 5/1999 | Arless et al. |
| 5,902,289 | A | 5/1999 | Swartz et al. |
| 5,902,300 | A * | 5/1999 | Hahnen et al. ............... 606/46 |
| 5,904,711 | A | 5/1999 | Flom et al. |
| 5,906,580 | A | 5/1999 | Kline-Schoder et al. |
| 5,906,587 | A | 5/1999 | Zimmon |
| 5,906,606 | A | 5/1999 | Chee et al. |
| 5,908,029 | A | 6/1999 | Knudson et al. |
| 5,913,854 | A | 6/1999 | Maguire et al. |
| 5,916,213 | A | 6/1999 | Haissaguerre et al. |
| 5,916,214 | A | 6/1999 | Cosio et al. |
| 5,921,924 | A | 7/1999 | Avitall |
| 5,921,982 | A | 7/1999 | Lesh et al. |
| 5,925,045 | A | 7/1999 | Reimels et al. |
| 5,927,284 | A | 7/1999 | Borst et al. |
| 5,928,191 | A | 7/1999 | Houser et al. |
| 5,931,810 | A | 8/1999 | Grabek |
| 5,931,848 | A | 8/1999 | Saadat |
| 5,935,123 | A | 8/1999 | Edwards et al. |
| 5,944,715 | A | 8/1999 | Goble et al. |
| 5,954,661 | A | 9/1999 | Greenspon et al. |
| 5,957,919 | A | 9/1999 | Laufer |
| 5,971,980 | A | 10/1999 | Sherman |
| 5,971,983 | A | 10/1999 | Lesh |
| 5,980,516 | A | 11/1999 | Mulier et al. |
| 5,989,248 | A | 11/1999 | Tu et al. |
| 5,993,412 | A | 11/1999 | Deily et al. |
| 5,993,447 | A | 11/1999 | Blewett et al. |
| 6,004,316 | A | 12/1999 | Laufer |
| 6,004,319 | A | 12/1999 | Goble et al. |
| 6,007,499 | A | 12/1999 | Martin et al. |
| 6,010,500 | A | 1/2000 | Sherman et al. |
| 6,012,457 | A | 1/2000 | Lesh |
| 6,015,391 | A | 1/2000 | Rishton et al. |
| 6,016,811 | A | 1/2000 | Knopp et al. |
| 6,018,676 | A | 1/2000 | Davis et al. |
| 6,019,757 | A | 2/2000 | Scheldrup |
| 6,024,733 | A | 2/2000 | Eggers et al. |
| 6,030,381 | A | 2/2000 | Jones et al. |
| 6,036,687 | A | 3/2000 | Laufer et al. |
| 6,036,698 | A * | 3/2000 | Fawzi et al. ............... 606/114 |
| 6,042,556 | A | 3/2000 | Beach et al. |
| 6,048,333 | A | 4/2000 | Lennox et al. |
| 6,056,744 | A | 5/2000 | Edwards |
| 6,056,745 | A | 5/2000 | Panescu et al. |
| 6,056,746 | A | 5/2000 | Goble |
| 6,056,747 | A | 5/2000 | Saadat et al. |
| 6,063,081 | A | 5/2000 | Mulier |
| 6,066,139 | A | 5/2000 | Ryan et al. |
| 6,068,653 | A | 5/2000 | LaFontaine |
| 6,071,279 | A | 6/2000 | Whayne et al. |
| 6,083,237 | A | 7/2000 | Huitema et al. |
| 6,086,585 | A | 7/2000 | Hovda et al. |
| 6,088,894 | A | 7/2000 | Oakley |
| 6,096,037 | A | 8/2000 | Mulier |
| 6,113,592 | A | 9/2000 | Taylor |
| 6,113,596 | A | 9/2000 | Hooven et al. |
| 6,117,101 | A | 9/2000 | Diederich et al. |
| 6,120,496 | A | 9/2000 | Whayne et al. |
| 6,141,576 | A | 10/2000 | Littmann et al. |
| 6,142,993 | A | 11/2000 | Whayne et al. |
| 6,142,994 | A | 11/2000 | Swanson et al. |
| 6,149,620 | A | 11/2000 | Baker et al. |
| 6,152,920 | A | 11/2000 | Thompson et al. |
| 6,161,543 | A | 12/2000 | Cox et al. |
| 6,165,174 | A | 12/2000 | Jacobs et al. |
| 6,190,384 | B1 | 2/2001 | Ouchi |
| 6,193,716 | B1 | 2/2001 | Shannon, Jr. |
| 6,210,406 | B1 | 4/2001 | Webster |
| 6,210,410 | B1 | 4/2001 | Farin et al. |
| 6,210,411 | B1 | 4/2001 | Hofmann et al. |
| 6,212,426 | B1 | 4/2001 | Swanson |
| 6,216,704 | B1 | 4/2001 | Ingle et al. |
| 6,217,528 | B1 | 4/2001 | Koblish et al. |
| 6,217,576 | B1 | 4/2001 | Tu et al. |
| 6,224,592 | B1 | 5/2001 | Eggers et al. |
| 6,231,518 | B1 | 5/2001 | Grabek et al. |
| 6,231,591 | B1 | 5/2001 | Desai |
| 6,235,020 | B1 | 5/2001 | Cheng et al. |
| 6,235,024 | B1 | 5/2001 | Tu |
| 6,237,605 | B1 | 5/2001 | Vaska et al. |
| 6,238,347 | B1 | 5/2001 | Nix et al. |
| 6,238,387 | B1 | 5/2001 | Miller, III |
| 6,238,393 | B1 | 5/2001 | Mulier |
| 6,245,061 | B1 | 6/2001 | Panescu et al. |
| 6,245,064 | B1 | 6/2001 | Lesh et al. |
| 6,245,065 | B1 | 6/2001 | Panescu et al. |
| 6,251,092 | B1 | 6/2001 | Qin et al. |
| 6,251,110 | B1 | 6/2001 | Wampler |
| 6,251,128 | B1 | 6/2001 | Knopp et al. |
| 6,258,087 | B1 | 7/2001 | Edwards et al. |
| 6,264,650 | B1 | 7/2001 | Hovda et al. |
| 6,266,551 | B1 | 7/2001 | Osadchy et al. |
| 6,270,471 | B1 | 8/2001 | Hechel et al. |
| 6,283,988 | B1 | 9/2001 | Laufer et al. |

(56) References Cited

U.S. PATENT DOCUMENTS

| | | |
|---|---|---|
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,306,133 B1 | 10/2001 | Tu et al. |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli et al. |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,498 B1 | 2/2003 | Burbank et al. |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Hoey et al. |
| 6,558,382 B2 | 5/2003 | Jahns |
| 6,558,385 B1 | 5/2003 | McClurken et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,623,437 B2 | 9/2003 | Hinchliffe et al. |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson et al. |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,712,775 B2 | 3/2004 | Burbank et al. |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,156,845 B2 | 1/2007 | Mulier et al. |
| 7,166,106 B2 | 1/2007 | Bartel et al. |
| 7,189,231 B2 | 3/2007 | Clague et al. |
| 7,200,445 B1 | 4/2007 | Dalbec et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,329,267 B2 | 2/2008 | Weber |
| 7,361,175 B2 | 4/2008 | Suslov |
| 7,364,579 B2 | 4/2008 | Mulier et al. |
| 7,412,977 B2 | 8/2008 | Fields et al. |
| 7,537,595 B2 | 5/2009 | McClurken |
| 7,604,635 B2 | 10/2009 | McClurken et al. |
| 7,608,072 B2 | 10/2009 | Swanson |
| 7,628,789 B2 | 12/2009 | Soltesz et al. |
| 7,645,277 B2 | 1/2010 | McClurken et al. |
| 7,651,494 B2 | 1/2010 | McClurken et al. |
| 7,670,338 B2 | 3/2010 | Albrecht et al. |
| 7,691,050 B2 | 4/2010 | Gellman |
| 7,736,361 B2 | 6/2010 | Palanker |
| 7,770,584 B2 | 8/2010 | Danek et al. |
| 7,811,282 B2 | 10/2010 | McClurken |
| 7,815,634 B2 | 10/2010 | McClurken et al. |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | McClurken et al. |
| 8,105,323 B2 | 1/2012 | Buysse et al. |
| 8,172,828 B2 | 5/2012 | Chang et al. |

(56) References Cited

U.S. PATENT DOCUMENTS

| | | | |
|---|---|---|---|
| 8,177,783 B2 | 5/2012 | Davison et al. | |
| 8,216,233 B2 | 7/2012 | McClurken et al. | |
| 8,323,276 B2 | 12/2012 | Palanker et al. | |
| 8,348,946 B2 | 1/2013 | McClurken et al. | |
| 8,361,068 B2 | 1/2013 | McClurken | |
| 8,388,642 B2 | 3/2013 | Muni et al. | |
| 8,414,572 B2 | 4/2013 | Davison et al. | |
| 8,475,455 B2 | 7/2013 | McClurken | |
| 2002/0049483 A1 | 4/2002 | Knowlton | |
| 2002/0062131 A1 | 5/2002 | Gallo, Sr. | |
| 2002/0082634 A1 | 6/2002 | Kammerer et al. | |
| 2002/0100485 A1* | 8/2002 | Stevens et al. | 128/898 |
| 2003/0014050 A1 | 1/2003 | Sharkey et al. | |
| 2003/0032954 A1 | 2/2003 | Carranza et al. | |
| 2003/0045872 A1 | 3/2003 | Jacobs | |
| 2003/0045873 A1* | 3/2003 | Hinchliffe | 606/47 |
| 2003/0050635 A1 | 3/2003 | Truckai et al. | |
| 2003/0073993 A1 | 4/2003 | Ciarrocca | |
| 2003/0144656 A1 | 7/2003 | Ocel | |
| 2003/0191462 A1 | 10/2003 | Jacobs | |
| 2003/0204185 A1 | 10/2003 | Sherman et al. | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0024395 A1 | 2/2004 | Ellman et al. | |
| 2004/0044340 A1 | 3/2004 | Francischelli | |
| 2004/0049179 A1 | 3/2004 | Francischelli | |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0097920 A1* | 5/2004 | Desinger | 606/45 |
| 2004/0111136 A1 | 6/2004 | Sharkey et al. | |
| 2004/0111137 A1 | 6/2004 | Shankey et al. | |
| 2004/0116923 A1 | 6/2004 | Desinger | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0267326 A1 | 12/2004 | Ocel | |
| 2005/0010095 A1 | 1/2005 | Stewart et al. | |
| 2005/0020965 A1* | 1/2005 | Rioux et al. | 604/21 |
| 2005/0033280 A1 | 2/2005 | Francischelli | |
| 2005/0090815 A1 | 4/2005 | Francischelli | |
| 2005/0090816 A1 | 4/2005 | McClurken et al. | |
| 2005/0143729 A1 | 6/2005 | Francischelli | |
| 2005/0165392 A1 | 7/2005 | Francischelli | |
| 2005/0171525 A1 | 8/2005 | Rioux et al. | |
| 2005/0209564 A1 | 9/2005 | Bonner | |
| 2005/0267454 A1 | 12/2005 | Hissong | |
| 2005/0273097 A1 | 12/2005 | Ryan | |
| 2006/0009756 A1 | 1/2006 | Francischelli et al. | |
| 2006/0009759 A1 | 1/2006 | Chrisitian et al. | |
| 2006/0064085 A1 | 3/2006 | Schechter et al. | |
| 2006/0106375 A1 | 5/2006 | Werneth et al. | |
| 2006/0111709 A1 | 5/2006 | Goble et al. | |
| 2007/0049920 A1 | 3/2007 | McClurken et al. | |
| 2007/0093808 A1 | 4/2007 | Mulier et al. | |
| 2007/0118114 A1 | 5/2007 | Miller et al. | |
| 2007/0149965 A1 | 6/2007 | Gallo, Sr. et al. | |
| 2007/0208332 A1 | 9/2007 | Mulier et al. | |
| 2008/0015563 A1 | 1/2008 | Hoey et al. | |
| 2008/0058796 A1 | 3/2008 | O'Brien et al. | |
| 2008/0071270 A1 | 3/2008 | Desinger et al. | |
| 2008/0103494 A1 | 5/2008 | Rioux et al. | |
| 2008/0207028 A1 | 8/2008 | Schutz | |
| 2008/0243031 A1 | 10/2008 | Seibel et al. | |
| 2008/0262489 A1 | 10/2008 | Steinke | |
| 2009/0012513 A1 | 1/2009 | Utley et al. | |
| 2009/0054805 A1 | 2/2009 | Boyle, Jr. | |
| 2009/0182329 A1* | 7/2009 | Dycus | 606/48 |
| 2009/0264879 A1 | 10/2009 | McClurken et al. | |
| 2009/0264977 A1 | 10/2009 | Bruszewski et al. | |
| 2009/0306655 A1 | 12/2009 | Stangenes et al. | |
| 2010/0069904 A1 | 3/2010 | Cunningham | |
| 2010/0160906 A1 | 6/2010 | Jarrard | |
| 2010/0204560 A1 | 8/2010 | Salahieh et al. | |
| 2010/0241178 A1 | 9/2010 | Tilson et al. | |
| 2010/0274178 A1 | 10/2010 | LaPivert et al. | |
| 2011/0023888 A1 | 2/2011 | Vazales et al. | |
| 2011/0028965 A1 | 2/2011 | McClurken | |
| 2011/0137298 A1 | 6/2011 | Nguyen et al. | |
| 2011/0178515 A1 | 7/2011 | Bloom et al. | |
| 2011/0196367 A1 | 8/2011 | Gallo | |
| 2011/0295249 A1 | 12/2011 | Bloom et al. | |
| 2011/0319889 A1 | 12/2011 | Conley et al. | |
| 2012/0004657 A1 | 1/2012 | Conley et al. | |
| 2012/0071712 A1 | 3/2012 | Manwaring et al. | |
| 2012/0095461 A1 | 4/2012 | Herscher et al. | |
| 2012/0101496 A1 | 4/2012 | McClurken et al. | |
| 2012/0116397 A1 | 5/2012 | Rencher et al. | |
| 2012/0143293 A1 | 6/2012 | Mauch et al. | |
| 2012/0150165 A1 | 6/2012 | Conley et al. | |
| 2012/0157989 A1 | 6/2012 | Stone et al. | |
| 2012/0184983 A1 | 7/2012 | Chang et al. | |
| 2012/0191084 A1 | 7/2012 | Davison et al. | |
| 2012/0232553 A1 | 9/2012 | Bloom et al. | |
| 2012/0253343 A1 | 10/2012 | McClurken et al. | |

FOREIGN PATENT DOCUMENTS

| | | |
|---|---|---|
| WO | WO 99/05971 A1 | 2/1999 |
| WO | WO2007-037785 | 4/2007 |
| WO | WO 2009/108950 A2 | 9/2009 |
| WO | WO2010/141417 | 12/2010 |

OTHER PUBLICATIONS

Swedish Medical Center, Update, http://www.swedish.org/MediaFiles/Documents/HealthProfessionals/PhysPractice-Magazine/PPSEPT10, Sep. 2010, 7 pages.

Mark A. Gilger, Gastroenterologic Endoscopy in Children: Past, Present, and Future, Current Opinions in Pediatrics 13:429-434, http://sadieo.ucsf.edu/course/old/pre-2005/Pedendo.pdf, 2001, 6 pages.

Momem M. Wahidi et al., State of the Art*: Interventional Pulmonology, CHEST 131:261-274, http://chestjournal.chestpubs.org/content/131/1/261.full.pdf+html, 2007, 16 pages.

Kieran McManus, Developing a Thoracoscopic Surgical Service, available at http://web.mac.com/kieran.mcmanus/Chapters/General/Developing_VATS_program.html (no date available), last accessed Jun. 10, 2011, 28 pages.

\* cited by examiner

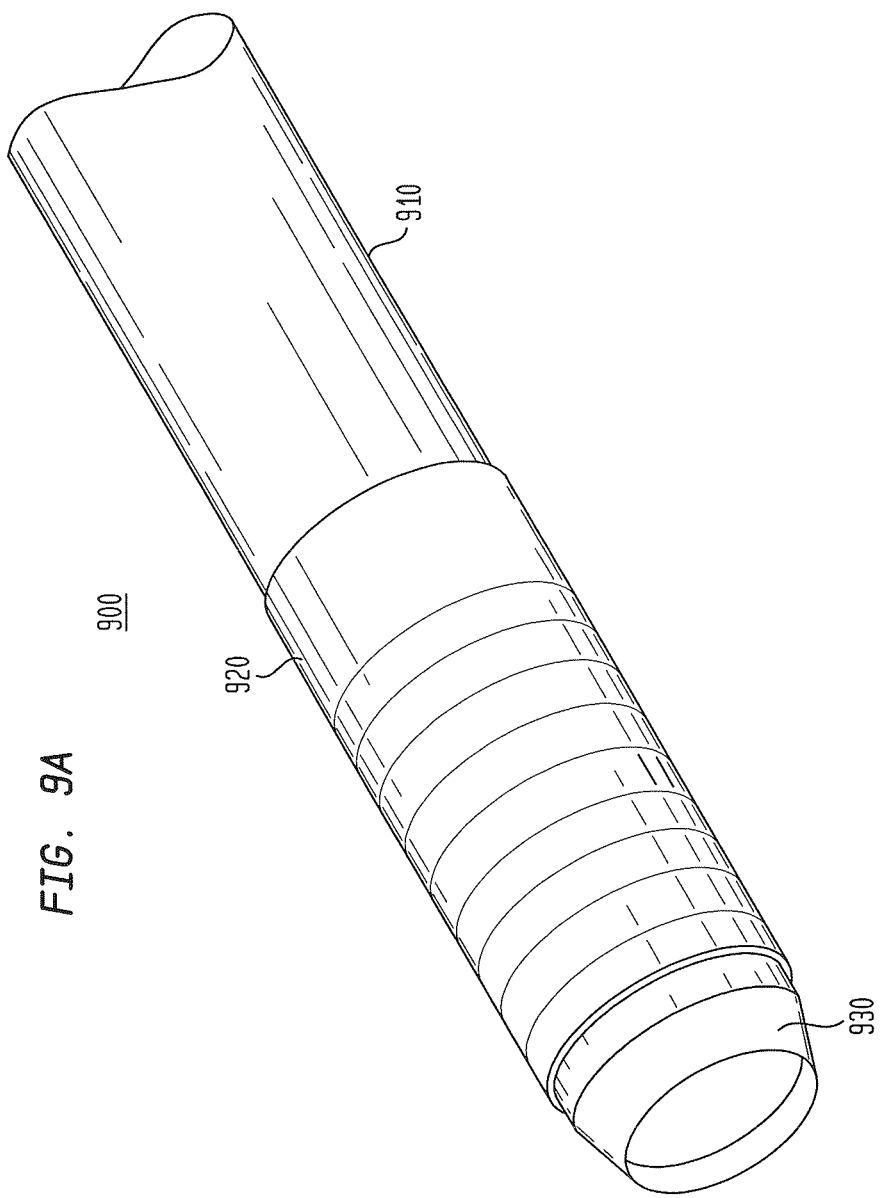

ELECTROSURGICAL CUTTING DEVICES

BACKGROUND

1. Field

The present invention relates to an electrosurgical device and, in particular, to a cutting device for use with a catheter device inserted into a body.

2. Background Art

Medicine is providing ever-increasing demands for devices that can navigate narrow passageways to a desired location within a body so that diagnostic and therapeutic procedures can be performed at that location. Currently, elongated medical devices such as catheters can extend into a body from outside via an access point through various connected passageways to a desired location. At this location, it is desirable that an electrosurgical procedure be one of the procedures that are made available.

An electrosurgical procedure involves a medical device that uses electrical energy to perform a procedure, such as coagulation, dissection, desiccation and cautery. The electrical energy can be provided in either direct current (DC) form or in alternating current (AC) form. However, low frequency electrical energy, including DC, can stimulate muscle and nerves and have potentially undesirable outcomes such as cardiac arrest, if not properly handled. Higher frequency electrical energy, and in particular electrical energy in the radiofrequency (RF) range, does not stimulate muscle or nerves, and can therefore be used to core and coagulate tissue.

Modern day elongated medical devices provide the ability for clinicians to navigate to remote and narrow locations within a body. To provide such access, these elongated medical devices must meet a wide variety of requirements such as a desired length and a sufficiently small outer diameter. Further, such a device must also have a sufficiently large inside diameter to permit navigation and delivery of the required functionality to the remote location. In the case of an RF-powered electrosurgical device located at the end of such an elongated medical device, the inside diameter needs to be both sufficiently large to transfer the required energy of the electrosurgical device, as well as provide sufficient diameter consistent with the aspiration requirements of the device. More specifically, sufficient electrical current needs to be delivered to support the RF power level desired at the particular location in the body. In the case of a coring procedure, the size of the inner diameter of the cutting device must also permit the required aspiration of cored tissue from that location. Further, it is necessary to ensure that the heat generated in the immediate vicinity of the cutting device be sufficiently isolated from the rest of the elongated medical device so that the elongated medical device does not deteriorate or self-destruct under the resulting thermal conditions.

BRIEF SUMMARY

What is needed is a cutting device suitable for coupling to an elongated medical device that can navigate a tortuous pathway within a body in a highly articulable fashion. In addition, it is desirable that the coupling from the elongated medical device to the cutting tip provide sufficient thermal isolation to permit operation without deterioration or self-destruction of distal portions of the elongated medical device.

In an embodiment of the present invention, a cutting device is provided that contains a substantially cylindrical body (e.g., ring) that has a peripheral cutting edge powered by electrical energy, such as RF energy, and is mechanically supported by one or more struts coupled to a catheter, but thermally isolated from the catheter. Thermal isolation is provided by inserting between the substantially cylindrical body and the catheter a material (e.g., air) that has a thermal resistance that is higher than the thermal resistance of the material (e.g., stainless steel) from which the substantially cylindrical body is formed. In one embodiment, an air gap is placed between the substantially cylindrical body (e.g., the ring) and the catheter. Thermal isolation can be further enhanced by the provision of slots in the ring. Additional thermal isolation can be provided by using slanted slots in the ring. The ring has an open interior that provides a channel for aspiration of the cored tissue. In further embodiments of the present invention, the open interior can be divided into four quadrants for separation of the tissue into four pieces, thereby allowing easier aspiration of the separated tissue.

In a further embodiment of the present invention, an RF-powered half-ring cutting device having a cutting edge is provided that is connected to one side of a catheter. On the opposing side of the catheter, an inflatable stabilization balloon is provided to provide mechanical support during operation of the cutting device. Lateral motion of the half-ring cutting edge results from external manipulation of the catheter that is coupled to the half-ring cutting edge. Thermal isolation is provided by use of thermally isolating materials at the junction between the half-ring cutting edge and the wire carrying the electrical current to the half-ring.

In a still further embodiment, an RF-powered substantially cylindrical body (e.g., ring) with cutting edge is connected via thermally insulating material to a catheter that includes a braided wire disposed within the catheter (either in the wall of the catheter or disposed in the lumen of the catheter). Electrical current is provided to the ring via one or more wires connected to the braided wire.

Further embodiments, features, and advantages of the invention, as well as the structure and operation of the various embodiments of the invention are described in detail below with reference to the accompanying drawings.

BRIEF DESCRIPTION OF THE DRAWINGS/FIGURES

Embodiments of the present invention are described with reference to the accompanying drawings. In the drawings, like reference numbers indicate identical or functionally similar elements.

Figure 7:
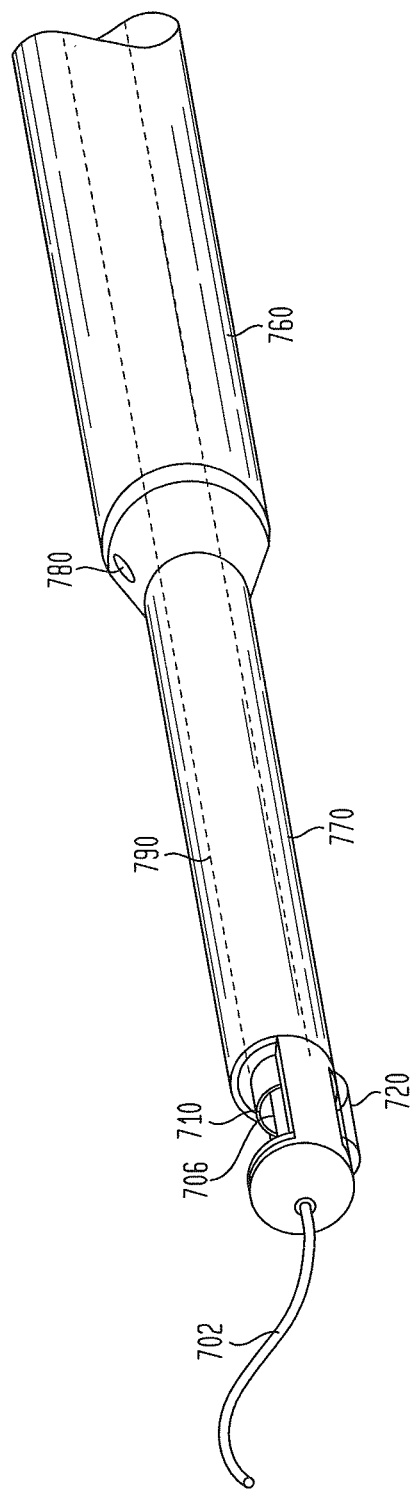

FIG. 7 and inset 7A illustrate a still further cutting device, in accordance with an embodiment of the present invention.

Figure 8:
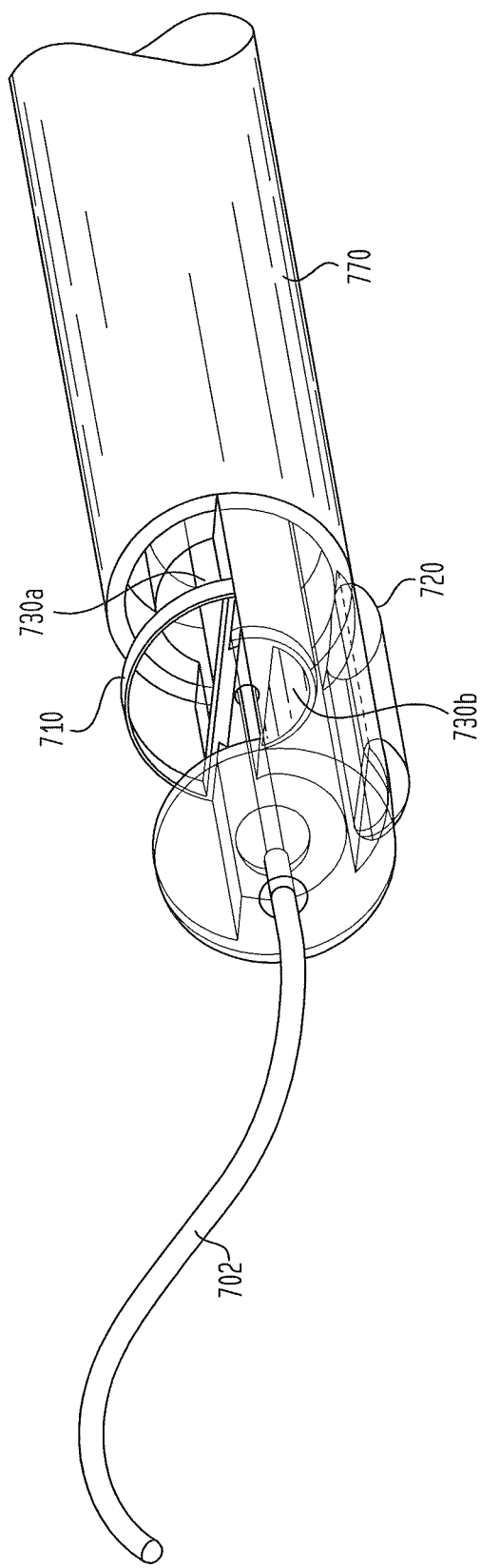

FIG. 8 illustrates a further view of the cutting device illustrated in FIG. 7.

Figure 9B:
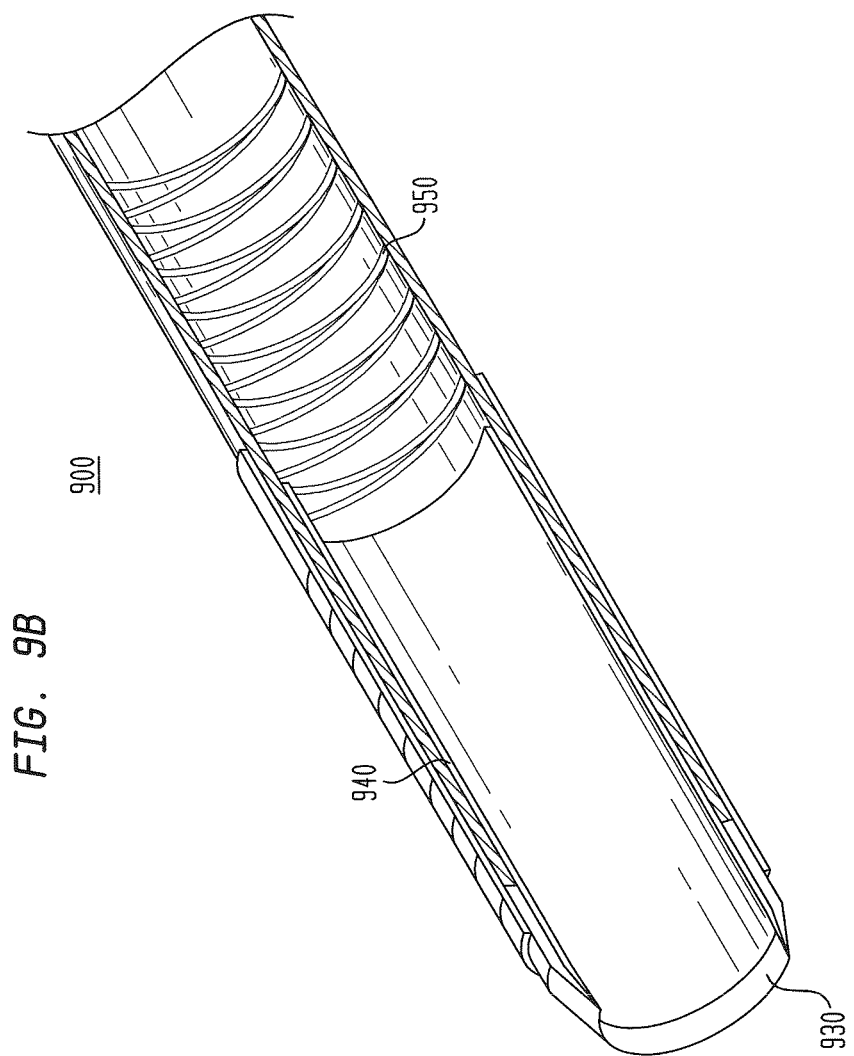

FIGS. 9A and 9B illustrate another cutting device, in accordance with an embodiment of the present invention.

Figure 10:
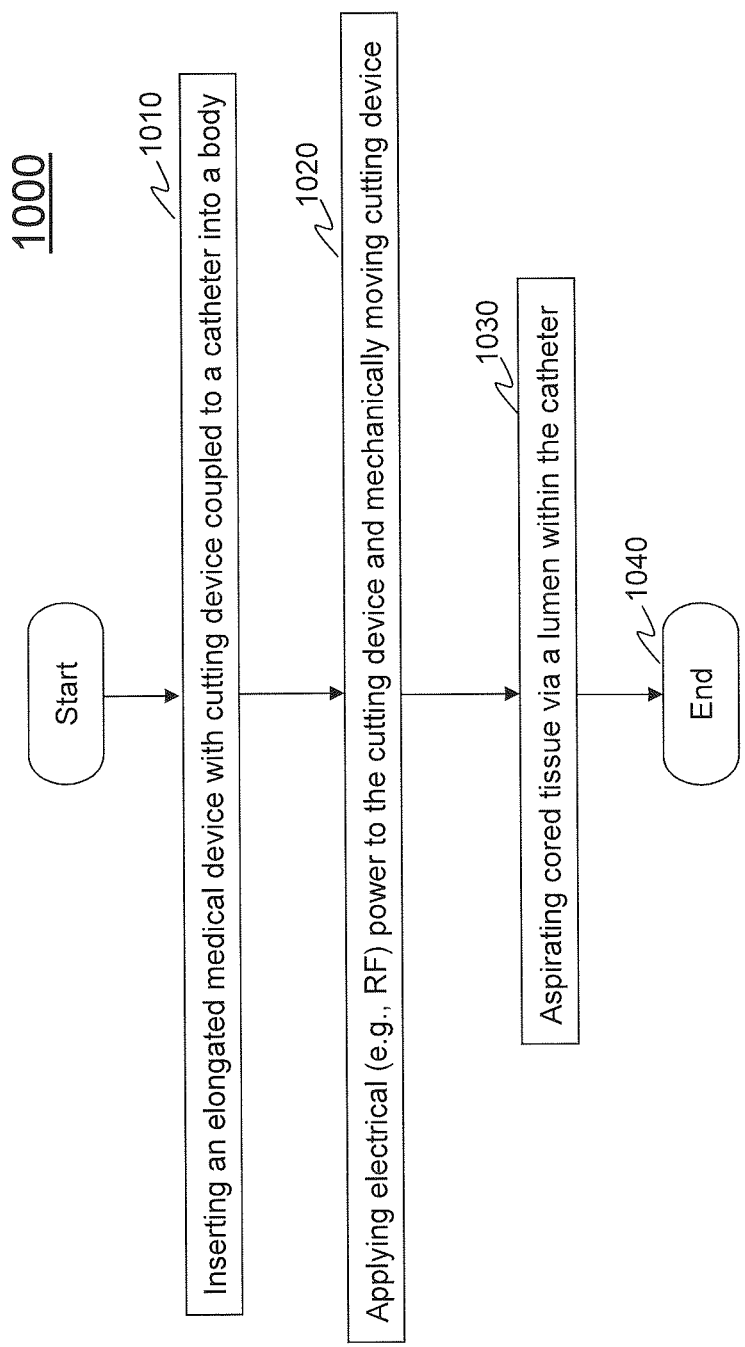

FIG. 10 provides a flowchart of a method for applying an RF-based electrosurgical procedure in a body using a cutting device, according to an embodiment of the current invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such a feature, structure, or characteristic in connection with other embodiments whether or not explicitly described.

Figure 1:
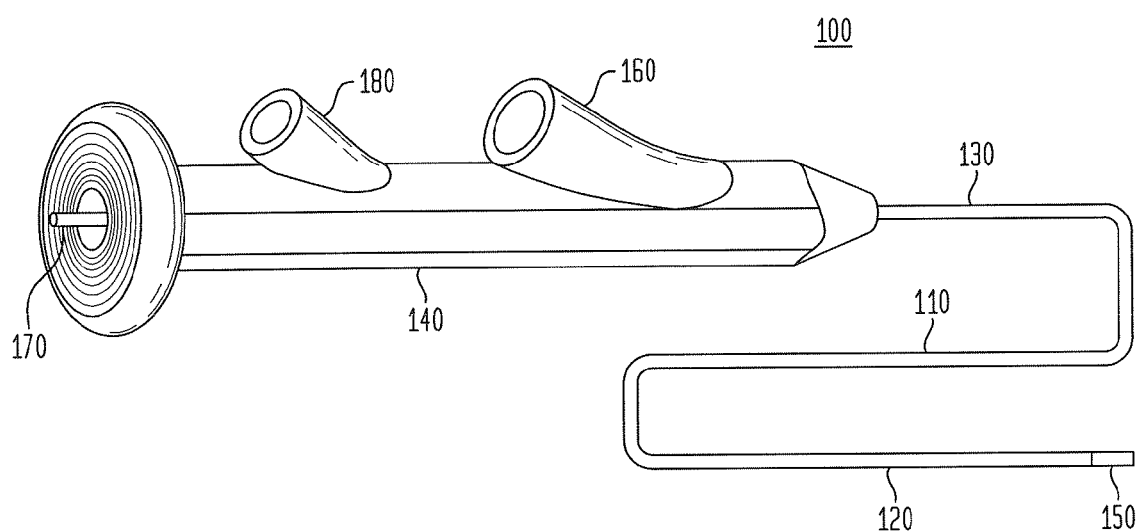
FIG. 1 illustrates an elongated medical device to which a cutting device can be coupled.

FIG. 1 depicts an example of a delivery device in the form of an elongated medical device 100, to which a cutting device (not shown) can be coupled. In exemplary embodiments, elongated medical device 100 is a flexible catheter or contains multiple flexible catheters. In various embodiments, elongated medical device 100 is an endoscope or other medical device. Elongated medical device 100 contains an elongated shaft 110 having a distal end 120 and a proximal end 130. Connected to proximal end 130 is a handle 140. Connected to distal end 120 is an interface 150 to the cutting device. Based on the location within the body for which access is sought, elongated shaft 110 can take on a wide variety of lengths. Ports 160, 170 and 180 provide access to one or more lumens of elongated medical device 100 to permit passage of other catheters or instruments (e.g., power to a cutting device, a vision system (e.g., fiber-optic device), an aspiration needle, a drug-delivery catheter, a biopsy instrument, a cutter, a balloon catheter, a electrocautery instrument, a hemostatic sealing instrument, etcetera). Some exemplary embodiments of elongated medical device 100 are described in U.S. patent application Ser. No. 12/862,677, filed Aug. 24, 2010 and entitled "Highly Articulable Catheter," which is incorporated herein by reference in its entirety.

Figure 2:
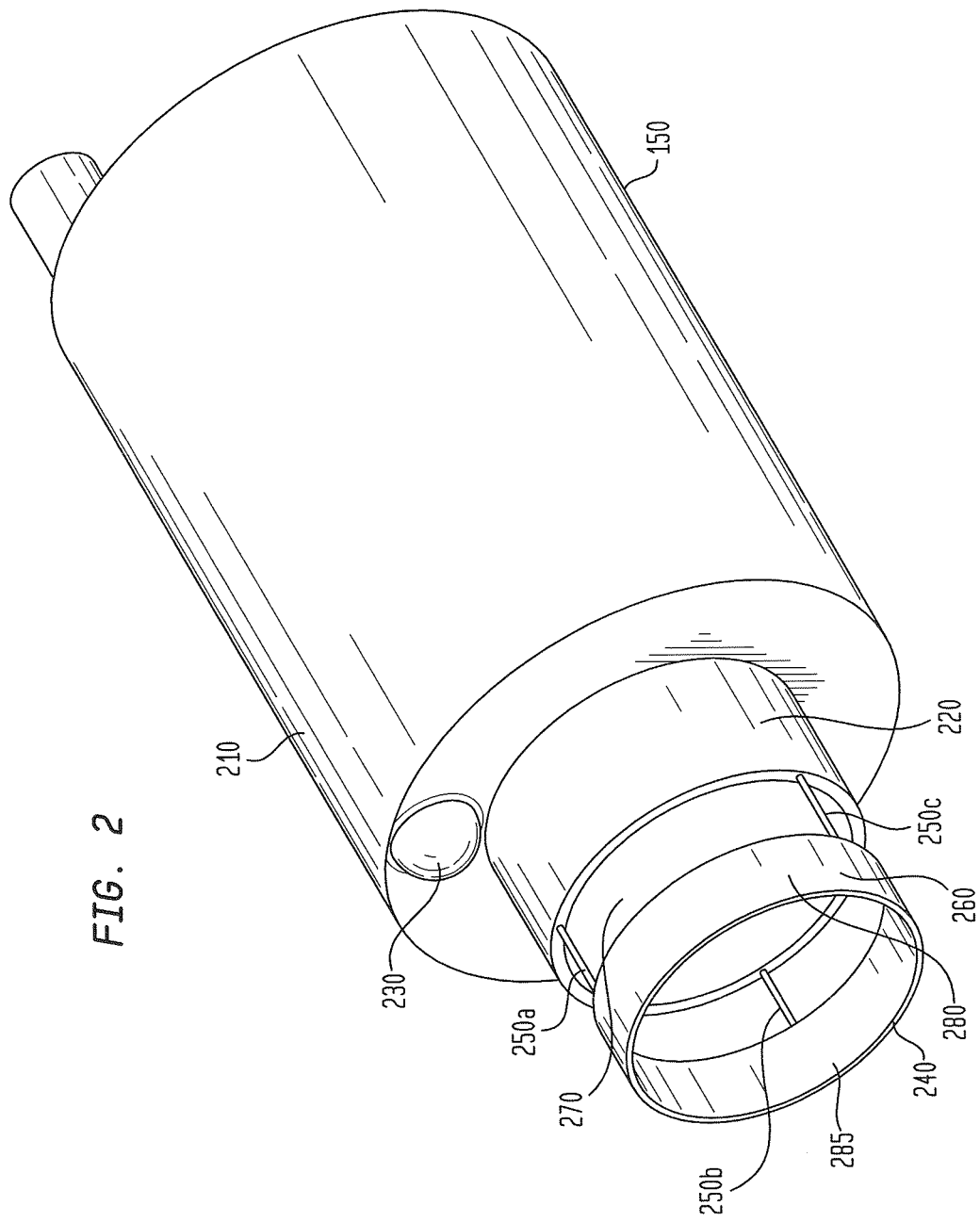
FIG. 2 illustrates a cutting device, in accordance with an embodiment of the present invention.

FIG. 2 depicts a cutting device 260, in accordance with an embodiment of the present invention. Interface 150 to the exemplary delivery device (elongated medical device 100) contains an outer catheter 210, inner catheter 220 and fiber optics 230. In this illustration, cutting device 260 is coupled to inner catheter 220 using one or more struts 250. Cutting device 260 is of a substantially cylindrical shape (e.g., ring-shaped) with a peripheral cutting edge 240. Struts 250 provide both mechanical support, as well as electrical connectivity, to cutting device 260. Struts 250 also provide a gap 270 between inner catheter 220 and cutting device 260, so that gap 270 provides a thermal barrier to prevent significant heat transfer from cutting device 260 back to inner catheter 220. In addition, struts 250 also provide sufficient open interior space so that aspirated tissue can be removed from the treatment site. In an exemplary embodiment, cutting device 260 has an outer diameter of about 2.5 mm (0.10 inches), a width (in the longitudinal direction of elongated medical device 100) of about 0.5-0.6 mm (0.020 to 0.025 inches), a wall thickness of about 0.125 mm (0.005 inches), and is separated by gap 270 of approximately 0.9 mm (0.035 inches). In other exemplary embodiments, cutting device 260 has ranges of dimensions such as an outer diameter of 2.3-3.2 mm (0.09-0.125 inches), a width of 0.5-1.9 mm (0.020 to 0.075 inches), a wall thickness of 0.0.8-0.5 mm (0.003-0.02 inches), and is separated by gap 270 of approximately 0.25-1.9 mm (0.01-0.075 inches).

In an exemplary embodiment of the present invention, three struts 250a, 250b, 250c are used to provide the coupling between cutting device 260 and inner catheter 220. Struts 250a, 250b, 250c are positioned so as to ensure sufficient mechanical stability in all three degrees of freedom for cutting device 260. Struts 250 extend into interface 150 and are mechanically secured therein. In the example embodiment described above, struts 250 can be approximately one inch in length, and thus the majority of the length of struts 250 is secured within interface 150. At least one of the struts 250 is connected (via welding or any other suitable method of securing) to a wire within a lumen in inner catheter 220, where the wire continues through the length of inner catheter 220 of elongated medical device 100 and finally emerges to be connected to an external electrical power supply. An exemplary electrical power supply is the Force FX™ RF electrosurgical generator that is manufactured by Valleylab, a division of Tyco Healthcare Group located in Boulder, Colo. With such an electrical connection, cutting device 260 is energized by the RF energy. Struts 250 can be made of any suitable material to provide the required mechanical strength and current carrying ability such as stainless steel.

In the exemplary embodiment shown in FIG. 2, cutting device 260 is a monopole device such that a return pad is required to be positioned on the body at a suitable location. Thus, electrical current such as RF current is emitted from cutting device 260 into the tissue immediately surrounding cutting device 260. From this tissue, the RF current propagates towards the return pad at which point the RF current converges at the return pad and exits the body.

Cutting device 260 can be made of stainless steel, although many other materials can be used consistent with the need to provide a suitable cutting edge 240, conduct electrical current such as electrical current in the RF frequency range, as well as handle the heat generated in the electrosurgical procedure. In a further embodiment, cutting edge 240 can be coated with silicone to avoid charring of the surrounding tissue, with the resulting difficulties posed by the aspiration of the charred tissue. In further additional optional embodiments, inner surface 285, outer surface 280, or both surfaces 280, 285 of cutting device 260 can be coated with silicone or a similar lubricious material. Coating inner surface 285 with a substance such as silicone facilitates a clean separation of tissue and subsequent tissue shrinkage, while coating outer surface 280 with silicone facilitates sliding in the immediate tissue environment. Silicone is one example of a coating. In fact, the coating can be any substance that provides either or both electrical insulation and thermal insulation. For example, a hydrophilic coating can be used to provide an electrically insulating layer, but not a thermally insulating layer. In a further embodiment, cutting device 260 can be used without any coating. For example, if hemostasis is desired, then no coating would be typically used, and the separated tissue will typically exhibit greater shrinkage than the shrinkage obtained with a coated embodiment. Depending on the electrosurgical procedure, the amount of RF power delivered to cutting device 260 can be, for example, up to 20 W. In a typical example, 20 W of RF power is delivered to cutting device 260.

Figure 3:
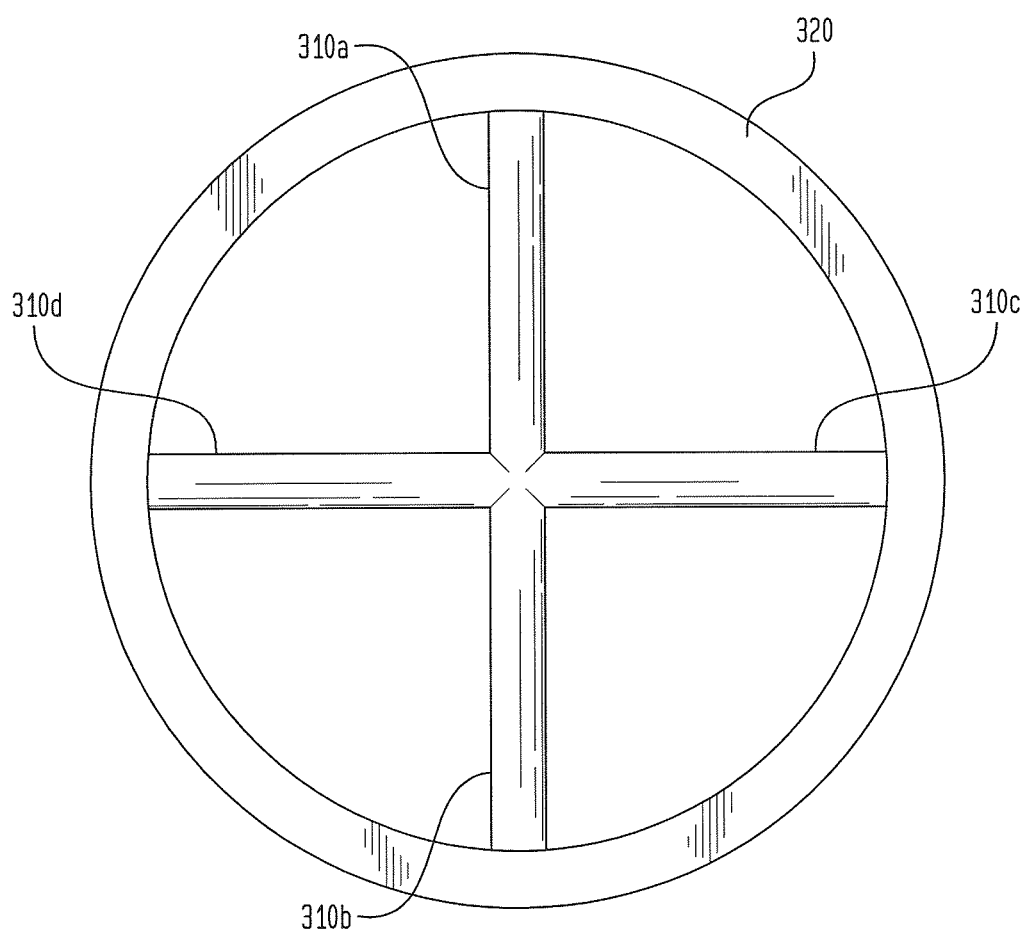
FIG. 3 illustrates a front view of the cutting device, in accordance with an embodiment of the present invention.

FIG. 3 illustrates a front view of another embodiment of cutting device 300. In this embodiment, cutting device 300 includes peripheral cutting edge 320 and cross-bars 310 (including cross-bar segments 310a, 310b, 310c, 310d) which are arranged to be orthogonal to one another to form four (4) sections. In an exemplary embodiment as shown in FIG. 3, the four sections can be equal, i.e., quadrants. Cross-bars 310 are electrically connected to cutting edge 320 and are also energized with electrical energy. Thus, cross-bars 310 also provide additional cutting surfaces and thus this embodiment provides additional cutting surface area beyond that shown in the embodiment in FIG. 2. The sections (e.g., quadrants) are open in the interior and therefore these sections enable the aspiration of the cored tissue. Other arrangements and numbers of struts can be used so that the inner space is broken into two or more sections, and thereby fall within the scope of the present invention. Further, as noted above, the two or more sections can be non-equal and fall within the scope of the present invention. Cross-bars 310 using similar materials as mentioned for cutting device 260, and include stainless steel.

Figure 4:
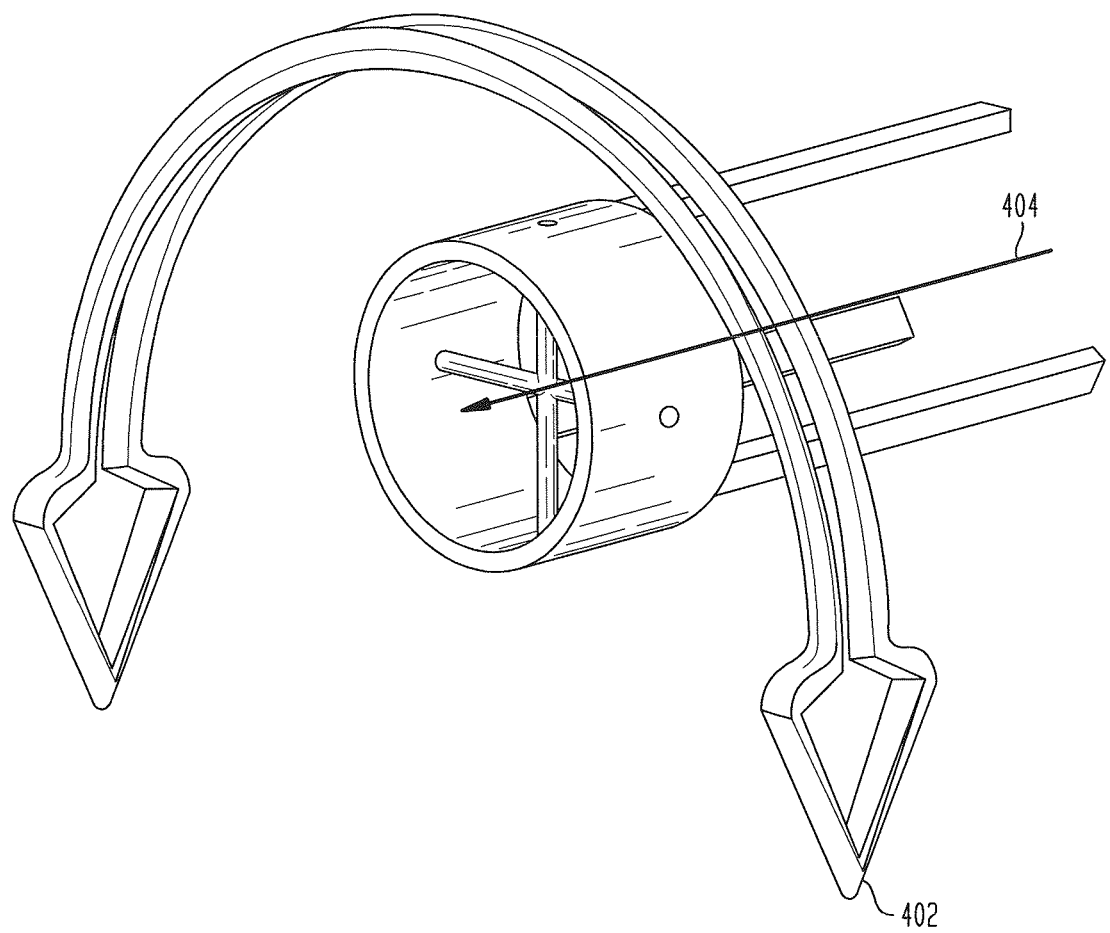
FIG. 4 illustrates a usage model of the cutting device, in accordance with an embodiment of the present invention.

FIG. 4 illustrates a usage model of a cutting device such as cutting device 300. As FIG. 4 illustrates, separation of tissue can be achieved by rotation of cutting device 300 in the direction indicated by arrows 402 while applying forward pressure in the direction indicated by arrow 404, in connection with delivery of RF energy. Rotation of cutting device 300 can be performed by external rotation of the proximal end of the catheter to which cutting device 300 is coupled, e.g., inner catheter 220. Tissue separation can be accomplished by rotation in either or both directions. Such rotation can be performed manually or automatically by a machine (e.g., a stepper motor). Upon separation of the tissue of interest, aspiration of the separated tissue proceeds by way of the interior of the sections of cutting device 300 and the interior of its attached catheter, e.g., inner catheter 220. Cutting device 300 and its rotational mode of use is particularly appropriate for longer portions of tissue removal that require tunneling forward over an extended length, with separation and aspiration as one moves forward. For removing relatively small portions of tissue, some forward pressure of cutting device 260 will often be sufficient without requiring rotation.

With respect to the thermal environment, significant heat is dissipated locally in the immediate vicinity of cutting devices 260, 300. Particularly vulnerable to the temperature increases is interface 150 of elongated medical device 100. In order to provide sufficient electrical energy to cutting devices 260, 300 without a resulting destruction of the cutting device, thermal considerations must be accommodated in the design. In an exemplary embodiment of cutting devices 260, 300, as noted above, a gap 270 (see FIG. 2) is provided in series between cutting devices 240, 300 and the catheter to which it is attached, e.g., inner catheter 220. The provision of gap 270 introduces additional thermal resistance and therefore heat is unable to travel as freely towards inner catheter 220. This helps to protect the stability and integrity of inner catheter 220 and elongated medical device 100. As noted above, in an exemplary embodiment, gap 270 is approximately 0.035 inches in width. Other dimensions can be used that are consistent with the need to provide a suitable thermal resistance between cutting devices 260, 300 and interface 150.

Figure 5:
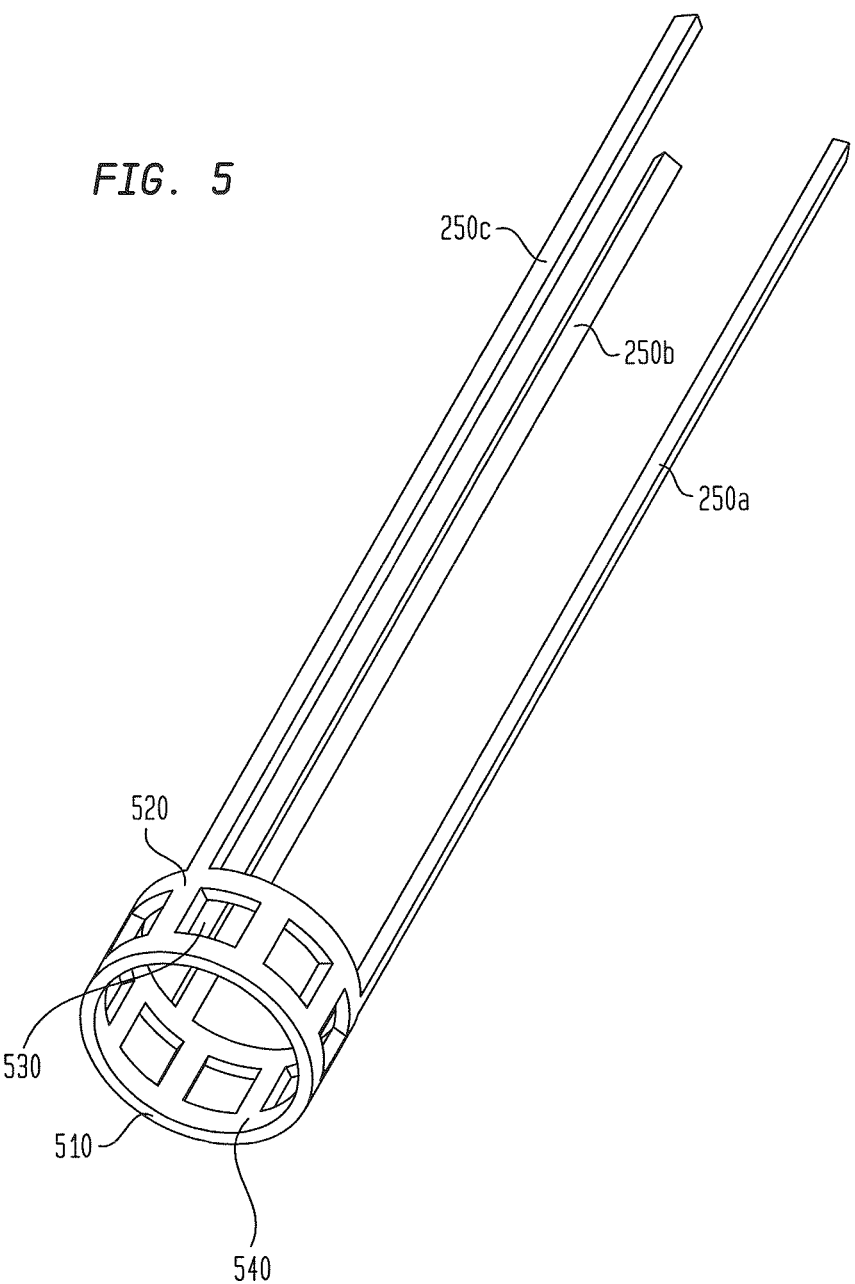
FIG. 5 illustrates another cutting device, in accordance with another embodiment of the present invention.

In an alternative thermal embodiment as shown in FIG. 5, increased thermal resistance can be further achieved by the use of slots or other openings in the substantially cylindrical portion (ring-portion) 520 of cutting device 540. For example, FIG. 5 shows cutting device 540 having slots 530 that reduce the amount of thermally conducting material in the thermal pathway between peripheral cutting edge 510 and inner catheter 220. Slots 530 decrease the ability for heat to travel from the heat source, namely cutting edge 510, towards inner catheter 220 (not shown in FIG. 5) via struts 250. Instead of a thermal path that consists of an entire ring, much of the metal has been removed to form slots 530, which thereby increases the thermal resistance. As known by one of ordinary skill in the relevant arts, increased thermal resistance diminishes the ability for heat to propagate to inner catheter 220, increased temperature effects are confined to cutting edge 510, and interface 150 and the rest of elongated medical device 100 is thereby protected from thermal damage. Example dimensions for slots 530 are: six slots having a width in the range of 0.13-0.76 mm (0.005-0.030 inches) and a length in the range of 0.13-0.76 mm (0.005-0.030 inches), although the number of slots and the dimensions can take on a wide range consistent with maintaining the structural integrity of substantially cylindrical portion 520 while providing an appropriate thermal resistance.

Figure 6:
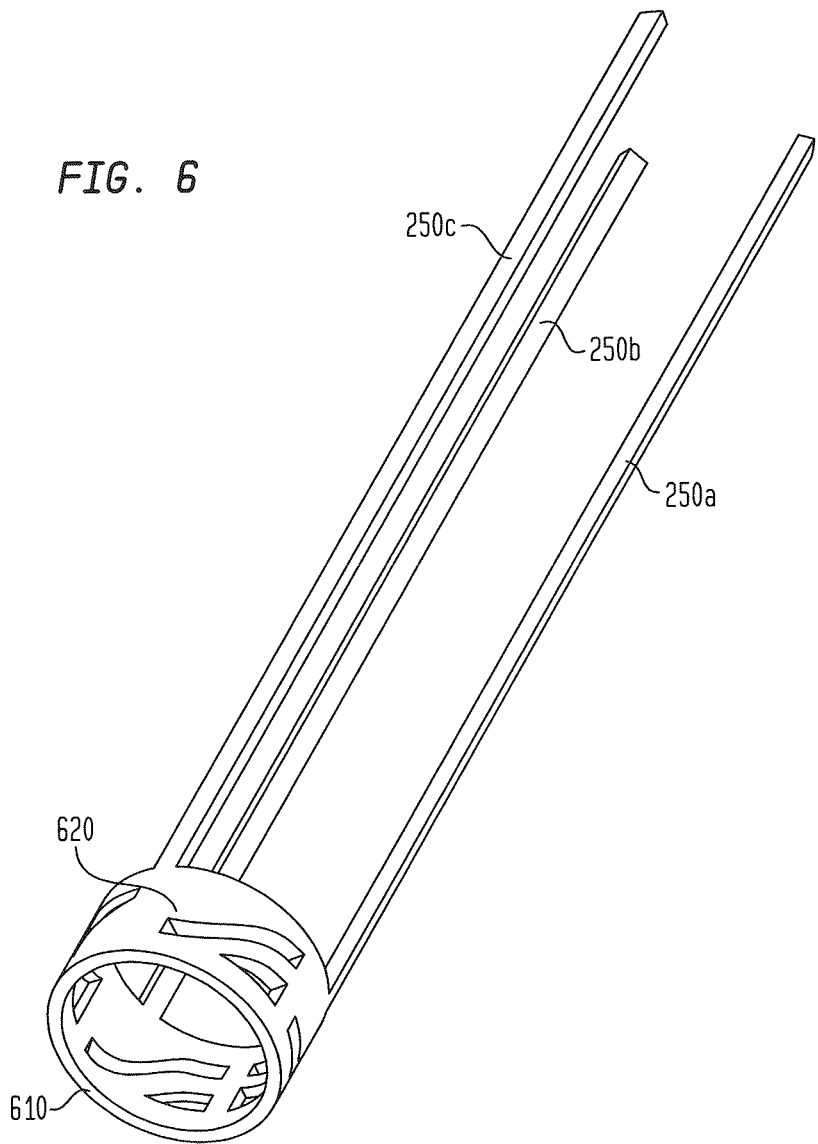
FIG. 6 illustrates still another cutting device, in accordance with another embodiment of the present invention.

In a still further embodiment, thermal resistance is increased using slanted slots 620, i.e., by placing the slots on an angle, as illustrated in FIG. 6. By placing slots 620 on an angle, the length of thermal path between the source of the heat at peripheral cutting edge 610 and the coupled catheter (e.g., inner catheter 220) via struts 250 is increased, which in turn raises the thermal resistance. Thus, for the same length of slot, slanted slots 620 lengthen the thermal path and thereby increase the thermal resistance. Example dimensions for slanted slots 620 are: six slots slanted at 30 degrees, having a width in the range of 0.13-0.76 mm (0.005-0.030 inches) and a length in the range of 1.3-7.1 mm (0.050-0.280 inches), although the number of slots, slant angle and the dimensions can take on a wide range consistent with maintaining the structural integrity of substantially cylindrical portion 620 while providing an appropriate thermal resistance.

In another embodiment of the present invention, FIG. 7 illustrates a cutting device 700 with a cutting edge 710 adapted to separate tissue located in a lateral or side direction from the axial or longitudinal direction of cutting device 700. As with the other embodiments, cutting device 700 can be coupled to elongated medical device 100. In this embodiment, elongated medical device 100 includes outer catheter 760, middle catheter 770, vision system 780, and inner catheter 790. Inner catheter 790 is within middle catheter 770, which in turn is within outer catheter 760. Vision system 230 is disposed within a lumen of outer catheter 760. Vision system 230 can be provided to facilitate illumination and viewing of the local surroundings of cutting device 700. As shown in FIG. 7, elongated medical device 100 can be positioned in a body passageway by advancing it over an optional guide wire 702 which extends through a lumen of inner catheter 790. Outer catheter 760 is retractable to expose cutting edge 710, as shown in FIG. 7. When navigating elongated medical device 100 in a body passageway, outer catheter 760 would be in the non-retracted position so that cutting edge 710 is covered. Outer catheter 760 can be externally manipulated by a clinician at proximal end of elongated medical device 100. Such manipulation can be either manual or through some automated means.

Cutting edge 710 is coupled to inner catheter 790, and is located on a side of cutting device 700. On the opposite side of cutting device 700 is a stabilization balloon 720. Cutting edge 710 can be any shape but is typically semi-circular, or a portion thereof, and is moveable in a longitudinal direction. In an open position, cutting device 700 includes a cavity 706 coupled to a lumen within inner catheter 790 for aspiration of separated tissue. Tissue is separated when cutting edge 710 moves to the closed position (i.e., in a longitudinal direction away from proximal end 130 of elongated medical device 100 and moves against the tissue of interest. To facilitate such manipulation between the open position and closed position of cutting edge 710, cutting edge 710 is coupled to inner catheter 790. Inner catheter 790 can be manipulated by a clinician at the proximal end of elongated medial device 100. Such manipulation of cutting edge 710 can be either manual or via some automated means.

Figure 7A:
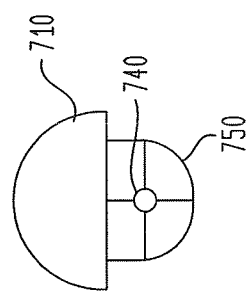

Cutting edge 710 is provided energy via a conductor or wire 740, as illustrated in the cross-section view in inset FIG. 7A. Providing thermal resistance is support structure 750 that provides support for wire 740 and is connected to cutting edge 710. Wire 740 is electrically connected to cutting edge 710, while support structure 750 provides the mechanical coupling between cutting edge 710 and inner catheter 790. Support structure 750 can be made of any material that provides sufficient mechanical support but high thermal resistance. Such a material includes bakelite. Wire 740 is disposed within a lumen within inner catheter 790 and finally out to an external electrical power supply (not shown), e.g. an RF power supply. As before, an exemplary RF power supply is the Force FX™ electrosurgical generator manufactured by Valleylab, a division of Tyco Healthcare Group located in Boulder, Colo. Cutting edge 710 can be made of stainless steel, although many other materials can be used consistent with the need to provide a suitable cutting surface, conduct RF electrical current, as well as handle the heat generated in the electrosurgical procedure. Cutting edge 710 can be coated with silicone to avoid charring of the surrounding tissue, with the resulting difficulties in aspiration the charred tissue.

On the opposing side of inner catheter is a stabilization balloon 720. Stabilization balloon 720 is coupled via a lumen within middle catheter 770 to a source of gas (such as air) or fluid (such as saline) that can be used for inflation. Inflation of stabilization balloon 720 applies a force that ensures cutting edge 710 is positioned or wedged against the tissue of interest. Then, the clinician manipulates the energized cutting edge 710 as noted above. Separate tissue can be aspirated via a lumen within inner catheter 790. Example dimensions for cutting edge 710 are about 0.25 mm (0.010 inches) in diameter, about 0.50 mm (0.020 inches) in width, with about 0.13 mm (0.005 inches) in thickness. Example dimensions for stabilization balloon 720 are about 5.1 mm (0.20 inches) in length. Stabilization balloon 720 can be made of any suitable material to provide repetitive inflation and deflation in a biocompatible manner, and such materials include silicone.

FIG. 8 provides a further view of cutting device 700. Aspiration ports 730A and 730B are shown inside inner catheter 790 whereby cored tissue can be aspirated into one or more lumens within inner catheter 790.

FIGS. 9A and 9B illustrate a further embodiment of a cutting device 900. Cutting device 900 can be connected to an inner catheter of elongated medical device 100. Cutting device 900 includes an interface section 910, followed by a thermally insulating section 920, which in turn is followed by a cutting tip 930. Interface section 910 can include an outer surface coating using a thermoplastic elastomer such as polyether block amide (e.g., PEBAX™). Thermally insulating section 920 includes one or more segments of a thermally insulating material. Thermally insulating section 920 can be composed of any thermally insulating material such as polyimide. Thermally insulating section 920 provides a thermal resistance that limits the conduction of heat from cutting tip 930 to the succeeding sections such as interface section 910, and elongated medical device 100. On the internal side of thermally insulating section 920 is a liner made from a material such as fluorinated ethylene propylene (FEP), a fluorocarbon-based plastic with good electrical insulating properties and chemical and heat resistance. Other materials with similar properties can also be used. Cutting edge 930 receives electrical energy (e.g., RF energy) via one or more wires 940 coupled to braided wire that forms a part of (or is disposed within a lumen of) the inner catheter of elongated medical device 100. Coring of tissue occurs by forward longitudinal motion of cutting tip 900. As before, cutting edge 930 can be coated with silicone to avoid charring of the surrounding tissue, with the resulting difficulties in aspiration the charred tissue. Example dimensions of cutting tip 930 are an inner diameter approximately that of the inner diameter of the inner catheter of elongated medical device 100, a length less than about 2.5 mm (0.1 inches) and a wall thickness similar to the wall thickness of the inner catheter of elongated medical device 100.

Embodiments of the present invention can be realized in the foam of various endoscopes and other catheter-based devices to support electrosurgical medical procedures in pulmonology, cardiology, urology, gastroenterology and neurology, or any procedure involving a hollow organ. Access by the present invention to the desired site within the body can be by any natural orifice, small incision or through the use of any minimally invasive surgery in order to perform the desired task. Such access points include but are not limited to mouth, nose, urethra, and radial, jugular and femoral arteries. Lengths of the elongated medical device 100 (to which various cutting devices can be attached) can range from 1 cm (as would be applicable in certain brain procedures), to a 5 cm length bronchoscope for use in a procedure on a small infant, to lengths in excess of 130 cm for use in various scopes such as endoscopes and bronchoscopes for adult procedures. In a one example embodiment for use in a flexible bronchoscope, elongated shaft 110 would be about 62.5 to 125 cm (25 to 50 inches) long, with outer catheter 210 having an outer diameter of about 4.2 mm and an inner diameter about 2.8 mm and inner catheter 220 having an outer diameter of about 2.7 mm and a lumen with an inner diameter of about 2.6 mm.

FIG. 10 provides a flowchart of an exemplary method 1000 to provide a method for coring tissue at a desired position within a body, according to an embodiment of the present invention.

The process begins at step 1010. In step 1010, an elongated medical device 100 having an outer catheter 210 and an inner catheter 220 is inserted into a body and navigated to the desired position for an electrosurgical procedure using a cutting device as disclosed herein.

In step 1020, RF power is applied to the cutting device and tissue is cored by mechanical manipulation of the cutting edge. Mechanical manipulation proceeds by way of forward motion of cutting device 260, rotation of cutting device 300, by to-and-fro motion of cutting device 700, or by way of forward motion of cutting tip 930.

In step 1030, aspiration of the cored tissue occurs via a lumen within the associated catheter, e.g., inner catheter 220.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An electrosurgical cutting device comprising:
a substantially cylindrical body having a first end and a second end, the first end defining a peripheral cutting edge defining a closed loop, the substantially cylindrically body further comprises at least one cross-bar disposed within an interior of the substantially cylindrical body; and
a plurality of struts extending longitudinally from the second end of the substantially cylindrical body and configured for mating with a delivery device to form a gap between the electrosurgical cutting device and the delivery device.

2. The electrosurgical cutting device of claim 1, wherein the substantially cylindrical body comprising at least one cross-bar disposed within an interior of the substantially cylindrical body comprises two cross-bars dividing the interior of the substantially cylindrical body into four quadrants.

3. The electrosurgical cutting device of claim 1, wherein the substantially cylindrical body comprises stainless steel.

4. The electrosurgical cutting device of claim 3, wherein the substantially cylindrical body comprises a silicone coating.

5. A medical device comprising:
a catheter having a distal end and a proximal end;
an electrosurgical cutting device attached to the distal end of the catheter, the electrosurgical cutting device comprising:
a substantially cylindrical body having a first end and a second end, the first end defining a peripheral cutting edge defining a closed loop, the substantially cylindrical body comprising one or more cross-bars disposed within an interior of the substantially cylindrical body,
a plurality of struts extending longitudinally from the second end of the substantially cylindrical body to attach the electrosurgical cutting device to the distal end of the catheter so as to form a gap between the electrosurgical cutting device and the catheter; and
an electrical conductor extending from the proximal end of the catheter to the distal end of the catheter for delivering electrical energy to the electrosurgical cutting device.

6. The apparatus of claim 5, wherein the substantially cylindrical body comprising one or more cross-bas disposed within an interior of the substantially cylindrical body comprises two cross-bars that divide the interior of the substantially cylindrical body into four quadrants.

7. The medical device of claim 5, wherein at least one of the plurality of struts is coupled to the electrical conductor.

8. The medical device of claim 5, wherein the electrical conductor is configured to deliver radio frequency energy.

9. The medical device of claim 5, wherein the plurality of struts comprises three or more struts configured to provide three dimensional mechanical stability for the electrosurgical cutting device.

10. The medical device of claim 5, wherein the substantially cylindrical body includes a coating on one or more surfaces.

11. The medical device of claim 10, wherein the coating comprises silicone.

12. The medical device of claim 10, wherein the coating comprises a hydrophilic substance.

13. A medical device comprising:
a catheter having a distal end and a proximal end;
an electrosurgical cutting device attached to the distal end of the catheter, the electrosurgical cutting device comprising:
a substantially cylindrical body having a first end and a second end, the first end defining a peripheral cutting edge defining a closed loop,
a plurality of struts extending longitudinally from the second end of the substantially cylindrical body to attach the electrosurgical cutting device to the distal end of the catheter so as to form a gap between the electrosurgical cutting device and the catheter; and
an electrical conductor extending from the proximal end of the catheter to the distal end of the catheter for delivering electrical energy to the electrosurgical cutting device, wherein the substantially cylindrical body comprises one or more slots disposed between the first end and the second end.

14. A medical device comprising:
a catheter having a distal end and a proximal end;
an electrosurgical cutting device attached to the distal end of the catheter, the electrosurgical cutting device comprising:
a substantially cylindrical body having a first end and a second end, the first end defining a peripheral cutting edge defining a closed loop,
a plurality of struts extending longitudinally from the second end of the substantially cylindrical body to attach the electrosurgical cutting device to the distal end of the catheter so as to form a gap between the electrosurgical cutting device and the catheter; and
an electrical conductor extending from the proximal end of the catheter to the distal end of the catheter for delivering electrical energy to the electrosurgical cutting device, wherein the substantially cylindrical body comprises one or more slanted slots.

* * * * *